United States Patent
Lettmann et al.

(10) Patent No.: US 8,870,876 B2
(45) Date of Patent: Oct. 28, 2014

(54) METHODS AND DEVICES FOR TREATING HALLUX VALGUS

(75) Inventors: Jason W. Lettmann, Menlo Park, CA (US); Joshua J. Baltzell, Palo Alto, CA (US)

(73) Assignee: Tarsus Medical Inc., Mountain View, CA (US)

( * ) Notice: Subject to any disclaimer, the term of this patent is extended or adjusted under 35 U.S.C. 154(b) by 826 days.

(21) Appl. No.: 12/371,354

(22) Filed: Feb. 13, 2009

(65) Prior Publication Data

US 2010/0211071 A1    Aug. 19, 2010

(51) Int. Cl.
*A61F 2/46*    (2006.01)

(52) U.S. Cl.
USPC ............ 606/86 R; 606/60; 606/328; 606/331

(58) Field of Classification Search
USPC .................................... 606/60, 328, 331, 908
See application file for complete search history.

(56) References Cited

U.S. PATENT DOCUMENTS

| | | |
|---|---|---|
| 2,291,413 A | 7/1942 | Siebrandt |
| 3,867,929 A | 2/1975 | Joyner et al. |
| 3,880,155 A | 4/1975 | Rosoff |
| 3,987,559 A | 10/1976 | Roberts |
| 4,069,824 A | 1/1978 | Weinstock |
| 4,213,208 A | 7/1980 | Marne |
| 4,240,214 A | 12/1980 | Sigle et al. |
| 4,244,359 A | 1/1981 | Dieterich |
| 4,255,875 A | 3/1981 | Gilkerson |
| 4,263,902 A | 4/1981 | Dieterich |
| 4,266,553 A | 5/1981 | Faiella |
| 4,300,294 A | 11/1981 | Riecken |
| 4,314,412 A | 2/1982 | Anderson et al. |
| 4,317,293 A | 3/1982 | Sigle et al. |
| 4,393,876 A | 7/1983 | Dieterich |
| 4,409,974 A | 10/1983 | Freedland |
| 4,414,964 A | 11/1983 | Farino et al. |
| 4,439,934 A | 4/1984 | Brown |
| 4,510,699 A | 4/1985 | Nakamura et al. |
| 4,583,303 A | 4/1986 | Laiacona et al. |
| 4,597,195 A | 7/1986 | Dananberg |
| 4,603,698 A | 8/1986 | Guttmann Cherniak |
| 4,604,997 A | 8/1986 | De Bastiani et al. |
| 4,608,988 A | 9/1986 | Dananberg |
| 4,632,103 A | 12/1986 | Fabricant et al. |

(Continued)

FOREIGN PATENT DOCUMENTS

| | | | |
|---|---|---|---|
| EP | 40782 | A2 | 12/1981 |
| EP | 60353 | A1 | 9/1982 |

(Continued)

OTHER PUBLICATIONS

Mini TightRope™ for Hallux Valgus Correction and Lisfranc Ligament Repair Surgical Technique, Anthrex, copyright 2007, 6 pp.
International Search Report and Written Opinion issued in PCT/US2010/023757, mailed Jun. 2, 2010, 16 pages.
Invitation to Pay Additional Fees issued in PCT/US2011/039041, mailed Sep. 6, 2011, 4 pages.

(Continued)

*Primary Examiner* — Andrew Yang
*Assistant Examiner* — Olivia C Chang
(74) *Attorney, Agent, or Firm* — Peter Matema; Eva Tan

(57) ABSTRACT

The various embodiments disclosed herein relate to implantable devices for the treatment of hallux valgus. More specifically, the various embodiments include devices having dynamic tensioning components or heat shrinkable components configured to urge two metatarsals together to treat a bone deformity.

20 Claims, 8 Drawing Sheets

(56) References Cited

U.S. PATENT DOCUMENTS

| | | |
|---|---|---|
| 4,644,940 A | 2/1987 | Nakamura |
| 4,676,801 A | 6/1987 | Lundeen |
| 4,726,127 A | 2/1988 | Barouk |
| 4,729,369 A | 3/1988 | Cook |
| 4,738,255 A | 4/1988 | Goble et al. |
| RE32,698 E | 6/1988 | Brown |
| 4,813,162 A | 3/1989 | Harris |
| 4,819,644 A | 4/1989 | Cherniak |
| 4,841,647 A | 6/1989 | Turucz |
| 4,842,931 A | 6/1989 | Zook |
| 4,852,556 A | 8/1989 | Groiso |
| 4,856,505 A | 8/1989 | Shaffer et al. |
| 4,876,758 A | 10/1989 | Rolloff et al. |
| 4,901,453 A | 2/1990 | Gaynor |
| 4,930,504 A | 6/1990 | Diamantopoulos et al. |
| 4,940,046 A | 7/1990 | Jacoby |
| 4,969,277 A | 11/1990 | Williams |
| 4,976,712 A | 12/1990 | VanderSlik |
| 5,005,575 A | 4/1991 | Geri |
| 5,012,596 A | 5/1991 | Schiller |
| 5,035,069 A | 7/1991 | Minden |
| 5,092,347 A | 3/1992 | Shaffer et al. |
| 5,094,226 A | 3/1992 | Medcalf et al. |
| 5,098,421 A | 3/1992 | Zook |
| 5,138,777 A | 8/1992 | Darby |
| 5,167,665 A | 12/1992 | McKinney |
| 5,174,052 A | 12/1992 | Schoenhaus et al. |
| 5,250,049 A | 10/1993 | Michael |
| D341,424 S | 11/1993 | Lurie |
| 5,272,139 A | 12/1993 | Cary, Jr. |
| 5,306,301 A | 4/1994 | Graf et al. |
| 5,350,383 A | 9/1994 | Schmieding et al. |
| RE34,753 E | 10/1994 | Groiso |
| 5,497,789 A | 3/1996 | Zook |
| 5,529,075 A | 6/1996 | Clark |
| 5,537,764 A | 7/1996 | Prahl |
| 5,539,020 A | 7/1996 | Bracken et al. |
| 5,571,139 A | 11/1996 | Jenkins, Jr. |
| 5,601,565 A | 2/1997 | Huebner |
| 5,607,756 A | 3/1997 | Yamauchi et al. |
| 5,611,801 A | 3/1997 | Songer |
| 5,617,651 A | 4/1997 | Prahl |
| 5,640,779 A | 6/1997 | Rolloff et al. |
| 5,645,588 A | 7/1997 | Graf et al. |
| 5,665,060 A | 9/1997 | Fabricant |
| 5,665,112 A | 9/1997 | Thal |
| 5,685,834 A | 11/1997 | Barth |
| H1706 H | 1/1998 | Mason |
| 5,713,903 A | 2/1998 | Sander et al. |
| 5,725,585 A | 3/1998 | Zobel |
| 5,728,136 A | 3/1998 | Thal |
| 5,788,697 A | 8/1998 | Kilpela et al. |
| 5,792,093 A | 8/1998 | Tanaka |
| 5,797,913 A | 8/1998 | Dambreville et al. |
| 5,802,737 A | 9/1998 | Beppu |
| 5,810,822 A | 9/1998 | Mortier |
| 5,843,085 A | 12/1998 | Graser |
| 5,853,293 A | 12/1998 | Weber et al. |
| 5,919,194 A | 7/1999 | Anderson |
| 5,921,986 A | 7/1999 | Bonutti |
| 5,962,011 A | 10/1999 | DeVillez et al. |
| 6,001,101 A | 12/1999 | Augagneur et al. |
| 6,068,648 A | 5/2000 | Cole et al. |
| 6,091,000 A | 7/2000 | Haynes |
| 6,093,163 A | 7/2000 | Chong et al. |
| 6,203,545 B1 | 3/2001 | Stoffella |
| 6,238,357 B1 | 5/2001 | Kawaguchi et al. |
| D443,694 S | 6/2001 | Ford |
| 6,248,109 B1 | 6/2001 | Stoffella |
| 6,248,788 B1 | 6/2001 | Robbins et al. |
| 6,264,677 B1 | 7/2001 | Simon et al. |
| 6,283,973 B1 | 9/2001 | Hubbard et al. |
| 6,315,749 B1 | 11/2001 | Sunayama |
| 6,318,373 B1 | 11/2001 | Kasahara |
| 6,319,270 B1 | 11/2001 | Grafton et al. |
| 6,348,053 B1 | 2/2002 | Cachia |
| 6,367,087 B1 | 4/2002 | Spillman et al. |
| 6,391,031 B1 | 5/2002 | Toomey |
| 6,406,234 B2 | 6/2002 | Frigg |
| 6,424,864 B1 | 7/2002 | Matsuura |
| 6,447,783 B1 | 9/2002 | Yayon |
| 6,478,761 B2 | 11/2002 | Bracamonte-Sommer |
| 6,481,120 B1 | 11/2002 | Xia et al. |
| 6,514,222 B2 | 2/2003 | Cook |
| 6,547,792 B1 | 4/2003 | Tsuji et al. |
| 6,547,800 B2 | 4/2003 | Foerster et al. |
| 6,569,188 B2 | 5/2003 | Grafton et al. |
| 6,583,114 B2 | 6/2003 | Vickery |
| 6,604,301 B1 | 8/2003 | Manoli, II et al. |
| 6,616,665 B2 | 9/2003 | Grafton et al. |
| 6,629,943 B1 | 10/2003 | Schroder |
| 6,643,956 B2 | 11/2003 | Mawusi et al. |
| 6,684,532 B2 | 2/2004 | Greene et al. |
| 6,689,136 B2 | 2/2004 | Stoffella |
| 6,716,234 B2 | 4/2004 | Grafton et al. |
| 6,800,063 B2 | 10/2004 | Iwata |
| 6,862,481 B1 | 3/2005 | Demian |
| 6,874,258 B2 | 4/2005 | Clough et al. |
| 6,887,243 B2 | 5/2005 | Culbert |
| 6,887,259 B2 | 5/2005 | Lizardi |
| 6,889,088 B2 | 5/2005 | Demian |
| 6,890,333 B2 | 5/2005 | von Hoffmann et al. |
| 6,902,799 B2 | 6/2005 | Chikamori |
| 6,908,465 B2 | 6/2005 | von Hoffmann et al. |
| 6,909,513 B1 | 6/2005 | Fujita et al. |
| 6,910,287 B2 | 6/2005 | Truelsen |
| 6,942,668 B2 | 9/2005 | Padget et al. |
| 6,964,645 B1 | 11/2005 | Smits |
| 6,991,636 B2 | 1/2006 | Rose |
| 7,008,428 B2 | 3/2006 | Cachia et al. |
| 7,013,583 B2 | 3/2006 | Greene et al. |
| 7,055,268 B2 | 6/2006 | Ha |
| 7,056,885 B1 | 6/2006 | Jeffers et al. |
| 7,062,866 B2 | 6/2006 | Bussler |
| 7,070,601 B2 | 7/2006 | Culbert et al. |
| 7,097,647 B2 | 8/2006 | Segler |
| 7,141,545 B2 | 11/2006 | Pike et al. |
| 7,175,667 B2 | 2/2007 | Saunders et al. |
| 7,192,411 B2 | 3/2007 | Gobet et al. |
| 7,217,853 B2 | 5/2007 | Kulichikhin et al. |
| 7,253,266 B2 | 8/2007 | Shimkets et al. |
| 7,263,788 B2 | 9/2007 | Johnson |
| 7,266,910 B2 | 9/2007 | Ingimundarson |
| 7,270,644 B2 | 9/2007 | Ingimundarson |
| 7,276,244 B2 | 10/2007 | Radovic |
| 7,287,293 B2 | 10/2007 | Cook et al. |
| 7,291,175 B1 | 11/2007 | Gordon |
| 7,291,483 B2 | 11/2007 | Shimkets et al. |
| 7,325,323 B2 | 2/2008 | Katsu et al. |
| 7,326,211 B2 | 2/2008 | Padget et al. |
| 7,383,089 B2 | 6/2008 | Demian |
| 7,392,605 B2 | 7/2008 | Hatfield et al. |
| 7,396,338 B2 | 7/2008 | Huber et al. |
| 7,485,153 B2 | 2/2009 | Padmanabhan et al. |
| 7,493,810 B2 | 2/2009 | Walczyk et al. |
| 7,513,880 B2 | 4/2009 | Ingimundarson et al. |
| 7,572,258 B2 | 8/2009 | Stiernborg |
| 7,625,395 B2 | 12/2009 | Muckter |
| 7,875,058 B2 | 1/2011 | Holmes, Jr. |
| 2001/0027583 A1 | 10/2001 | Rothbart |
| 2001/0034956 A1 | 11/2001 | Mawusi et al. |
| 2002/0007134 A1 | 1/2002 | Bracamonte-Sommer |
| 2002/0022862 A1 | 2/2002 | Grafton et al. |
| 2002/0032466 A1 | 3/2002 | Grafton et al. |
| 2002/0056209 A1 | 5/2002 | Clough et al. |
| 2002/0058036 A1 | 5/2002 | Jeffers et al. |
| 2002/0062140 A1 | 5/2002 | Demian |
| 2002/0077281 A1 | 6/2002 | Vickery |
| 2002/0138026 A1 | 9/2002 | Cook |
| 2002/0162250 A1 | 11/2002 | Campbell et al. |
| 2002/0193309 A1 | 12/2002 | Yayon |
| 2003/0005601 A1 | 1/2003 | Kasahara |
| 2003/0023268 A1 | 1/2003 | Lizardi |
| 2003/0040750 A1 | 2/2003 | Stoffella |

(56) References Cited

U.S. PATENT DOCUMENTS

| | | |
|---|---|---|
| 2003/0045881 A1 | 3/2003 | Barouk et al. |
| 2003/0093920 A1 | 5/2003 | Greene et al. |
| 2003/0105193 A1 | 6/2003 | Wang |
| 2003/0134792 A1 | 7/2003 | Pike et al. |
| 2003/0148692 A1 | 8/2003 | Chikamori |
| 2003/0152637 A1 | 8/2003 | Chasin et al. |
| 2003/0172553 A1 | 9/2003 | Truelsen |
| 2003/0186433 A1 | 10/2003 | Shimkets et al. |
| 2003/0187372 A1 | 10/2003 | Iwata |
| 2003/0225356 A1 | 12/2003 | Kulichikhin et al. |
| 2004/0019308 A1 | 1/2004 | Chow |
| 2004/0031169 A1 | 2/2004 | Jensen et al. |
| 2004/0039319 A1 | 2/2004 | Calatayud Carral |
| 2004/0045194 A1 | 3/2004 | Kumai |
| 2004/0093746 A1 | 5/2004 | Varsallona |
| 2004/0103561 A1 | 6/2004 | Campbell et al. |
| 2004/0107604 A1 | 6/2004 | Ha |
| 2004/0123495 A1 | 7/2004 | Greene et al. |
| 2004/0127907 A1 | 7/2004 | Dakin et al. |
| 2004/0156931 A1 | 8/2004 | Burch et al. |
| 2004/0161481 A1 | 8/2004 | Burch et al. |
| 2004/0168329 A1 | 9/2004 | Ishimaru |
| 2004/0168353 A1 | 9/2004 | Bussler |
| 2004/0186182 A1 | 9/2004 | Burch et al. |
| 2004/0191338 A1 | 9/2004 | Burch et al. |
| 2004/0194348 A1 | 10/2004 | Campbell et al. |
| 2004/0194352 A1 | 10/2004 | Campbell et al. |
| 2004/0210234 A1 | 10/2004 | Coillard et al. |
| 2004/0243197 A1 | 12/2004 | Demian |
| 2005/0019436 A1 | 1/2005 | Burch et al. |
| 2005/0020690 A1 | 1/2005 | Burch et al. |
| 2005/0054959 A1 | 3/2005 | Ingimundarson |
| 2005/0054962 A1 | 3/2005 | Bradshaw |
| 2005/0055849 A1 | 3/2005 | Ha |
| 2005/0058734 A1 | 3/2005 | Burch et al. |
| 2005/0059873 A1 | 3/2005 | Glozman et al. |
| 2005/0060910 A1 | 3/2005 | Kaneda et al. |
| 2005/0061332 A1 | 3/2005 | Greenawalt et al. |
| 2005/0063971 A1 | 3/2005 | Jeffers et al. |
| 2005/0070909 A1 | 3/2005 | Egger et al. |
| 2005/0076536 A1 | 4/2005 | Hatfield et al. |
| 2005/0115116 A1 | 6/2005 | Pedersen et al. |
| 2005/0123567 A1 | 6/2005 | First |
| 2005/0158382 A1 | 7/2005 | Cruz et al. |
| 2005/0177084 A1 | 8/2005 | Green et al. |
| 2005/0187071 A1 | 8/2005 | Yamashita et al. |
| 2005/0197711 A1 | 9/2005 | Cachia |
| 2005/0202047 A1 | 9/2005 | Radovic |
| 2005/0208540 A1 | 9/2005 | Shimkets et al. |
| 2005/0228389 A1 | 10/2005 | Stiernborg |
| 2005/0229430 A1 | 10/2005 | Takaba |
| 2005/0229433 A1 | 10/2005 | Cachia |
| 2005/0241187 A1 | 11/2005 | Johnson |
| 2005/0251081 A1 | 11/2005 | McClanahan et al. |
| 2006/0002954 A1 | 1/2006 | Tabata et al. |
| 2006/0015102 A1 | 1/2006 | Toullec et al. |
| 2006/0030854 A1 | 2/2006 | Haines |
| 2006/0058796 A1 | 3/2006 | Hartdegen et al. |
| 2006/0064048 A1 | 3/2006 | Stano |
| 2006/0074434 A1 | 4/2006 | Wenstrom et al. |
| 2006/0079558 A1 | 4/2006 | Aberg et al. |
| 2006/0079559 A1 | 4/2006 | Aberg et al. |
| 2006/0081553 A1 | 4/2006 | Patterson et al. |
| 2006/0148903 A1 | 7/2006 | Burch et al. |
| 2006/0155233 A1 | 7/2006 | Huber et al. |
| 2006/0161090 A1 | 7/2006 | Lee |
| 2006/0162464 A1 | 7/2006 | Hayashi et al. |
| 2006/0178702 A1 | 8/2006 | Pierce et al. |
| 2006/0189914 A1 | 8/2006 | Slavitt |
| 2006/0201011 A1 | 9/2006 | Katsu et al. |
| 2006/0240105 A1 | 10/2006 | Devane et al. |
| 2006/0241066 A1 | 10/2006 | Tomita et al. |
| 2006/0241607 A1 | 10/2006 | Myerson et al. |
| 2006/0241608 A1 | 10/2006 | Myerson et al. |
| 2006/0247566 A1 | 11/2006 | Gobet et al. |
| 2006/0251721 A1 | 11/2006 | Cruz et al. |
| 2006/0258588 A1 | 11/2006 | Pike et al. |
| 2006/0264954 A1* | 11/2006 | Sweeney et al. ............... 606/73 |
| 2006/0264961 A1 | 11/2006 | Murray-Brown |
| 2006/0269628 A1 | 11/2006 | Burch et al. |
| 2006/0271077 A1 | 11/2006 | Graser |
| 2006/0276737 A1 | 12/2006 | Rose |
| 2006/0282231 A1 | 12/2006 | Kurashina et al. |
| 2007/0010818 A1 | 1/2007 | Stone et al. |
| 2007/0016205 A1 | 1/2007 | Beutter et al. |
| 2007/0016275 A1 | 1/2007 | Ferdinand |
| 2007/0033750 A1 | 2/2007 | Cook et al. |
| 2007/0036876 A1 | 2/2007 | Burch et al. |
| 2007/0051020 A1 | 3/2007 | Tajima et al. |
| 2007/0051376 A1 | 3/2007 | Kulichikhin et al. |
| 2007/0074334 A1 | 4/2007 | Steel |
| 2007/0074426 A1 | 4/2007 | Dorsey |
| 2007/0078518 A1 | 4/2007 | Lavi |
| 2007/0088341 A1 | 4/2007 | Skiba et al. |
| 2007/0094896 A1 | 5/2007 | Hatfield et al. |
| 2007/0128226 A1 | 6/2007 | Radovic |
| 2007/0131798 A1 | 6/2007 | Katsukawa et al. |
| 2007/0141020 A1 | 6/2007 | Barritault et al. |
| 2007/0197948 A1 | 8/2007 | Ingimundarson et al. |
| 2007/0204487 A1 | 9/2007 | Clough |
| 2007/0213296 A1 | 9/2007 | Zhang |
| 2007/0213308 A1 | 9/2007 | Lessem et al. |
| 2007/0214681 A1 | 9/2007 | Dezfouli |
| 2007/0225217 A1 | 9/2007 | Chappell et al. |
| 2007/0225703 A1 | 9/2007 | Schmitz et al. |
| 2007/0260252 A1 | 11/2007 | Schmitz et al. |
| 2007/0265296 A1 | 11/2007 | Dalton et al. |
| 2007/0265634 A1 | 11/2007 | Weinstein |
| 2007/0281906 A1 | 12/2007 | Dalton et al. |
| 2007/0282342 A1 | 12/2007 | Niederberger et al. |
| 2007/0299382 A1 | 12/2007 | Millet |
| 2008/0008777 A1 | 1/2008 | Radovic |
| 2008/0010856 A1 | 1/2008 | Hakkala |
| 2008/0014272 A1 | 1/2008 | Skolnick et al. |
| 2008/0027119 A1 | 1/2008 | Lippa et al. |
| 2008/0041169 A1 | 2/2008 | Walczyk et al. |
| 2008/0057068 A1 | 3/2008 | Dalton et al. |
| 2008/0065224 A1 | 3/2008 | Reigstad et al. |
| 2008/0076829 A1 | 3/2008 | Dalton et al. |
| 2008/0078628 A1 | 4/2008 | Christen |
| 2008/0081834 A1 | 4/2008 | Lippa et al. |
| 2008/0086139 A1 | 4/2008 | Bourke et al. |
| 2008/0086909 A1 | 4/2008 | Raspini |
| 2008/0086913 A1 | 4/2008 | Nawachi et al. |
| 2008/0102121 A1 | 5/2008 | Devane et al. |
| 2008/0113025 A1 | 5/2008 | Devane et al. |
| 2008/0139641 A1 | 6/2008 | Meyer |
| 2008/0141565 A1 | 6/2008 | Rini et al. |
| 2008/0147084 A1 | 6/2008 | Bleich et al. |
| 2008/0153780 A1 | 6/2008 | Meyer |
| 2008/0155731 A1 | 7/2008 | Kasahara |
| 2008/0200989 A1 | 8/2008 | Cachia |
| 2008/0208252 A1 | 8/2008 | Holmes |
| 2008/0216593 A1 | 9/2008 | Jacobsen et al. |
| 2008/0217816 A1 | 9/2008 | Hemmi et al. |
| 2008/0221697 A1 | 9/2008 | Graser |
| 2008/0229482 A1 | 9/2008 | Millet |
| 2008/0242646 A1 | 10/2008 | Lessem et al. |
| 2008/0248282 A1 | 10/2008 | Martin et al. |
| 2008/0260791 A1 | 10/2008 | Burch et al. |
| 2008/0262091 A1 | 10/2008 | Burch et al. |
| 2008/0263900 A1 | 10/2008 | Determe et al. |
| 2008/0280975 A1 | 11/2008 | Badul |
| 2008/0282580 A1 | 11/2008 | Ji-Woog |
| 2008/0287406 A1 | 11/2008 | Lessem |
| 2008/0287866 A1 | 11/2008 | Heller |
| 2008/0288019 A1 | 11/2008 | Heller |
| 2008/0294170 A1 | 11/2008 | O'Brien |
| 2008/0301977 A1 | 12/2008 | Roberts et al. |
| 2009/0005358 A1 | 1/2009 | Lessem |
| 2009/0012180 A1 | 1/2009 | Lange et al. |
| 2009/0036893 A1 | 2/2009 | Kartalian et al. |
| 2009/0043318 A1 | 2/2009 | Michel et al. |
| 2009/0054527 A1 | 2/2009 | Burch et al. |

(56) References Cited

U.S. PATENT DOCUMENTS

| | | |
|---|---|---|
| 2009/0062253 A1 | 3/2009 | Gahman et al. |
| 2009/0062359 A1 | 3/2009 | Burch et al. |
| 2009/0082466 A1 | 3/2009 | Babul |
| 2009/0082773 A1 | 3/2009 | Haines |
| 2009/0082874 A1 | 3/2009 | Cachia |
| 2009/0111792 A1 | 4/2009 | Burch et al. |
| 2009/0113759 A1 | 5/2009 | Heid |
| 2009/0117167 A1 | 5/2009 | Burch et al. |
| 2009/0118242 A1 | 5/2009 | Burch et al. |
| 2009/0133289 A1 | 5/2009 | Cantoni |
| 2009/0155614 A1 | 6/2009 | McLeod et al. |
| 2009/0157194 A1 | 6/2009 | Shikinami |
| 2009/0181098 A1 | 7/2009 | Garrett et al. |
| 2009/0192222 A1 | 7/2009 | Yao et al. |
| 2009/0198287 A1 | 8/2009 | Chiu |
| 2009/0209536 A1 | 8/2009 | Gahman et al. |
| 2009/0210010 A1 | 8/2009 | Strnad et al. |
| 2009/0215809 A1 | 8/2009 | Yao et al. |
| 2009/0216334 A1 | 8/2009 | Leibel |
| 2009/0222047 A1 | 9/2009 | Graham |
| 2009/0228049 A1 | 9/2009 | Park |
| 2009/0287246 A1 | 11/2009 | Cauldwell et al. |
| 2009/0291975 A1 | 11/2009 | Stern et al. |
| 2009/0292022 A1 | 11/2009 | Kowalski et al. |
| 2009/0292023 A1 | 11/2009 | Kowalski et al. |
| 2009/0306723 A1 | 12/2009 | Anapliotis et al. |
| 2010/0036430 A1 | 2/2010 | Hartdegen et al. |
| 2010/0152752 A1 | 6/2010 | Denove |
| 2011/0077656 A1 | 3/2011 | Sand et al. |
| 2011/0118780 A1 | 5/2011 | Holmes, Jr. |
| 2011/0178557 A1 | 7/2011 | Rush et al. |
| 2011/0224729 A1 | 9/2011 | Baker et al. |
| 2011/0301648 A1 | 12/2011 | Lofthouse et al. |
| 2012/0016426 A1 | 1/2012 | Robinson |
| 2012/0071935 A1 | 3/2012 | Keith et al. |
| 2012/0330322 A1 | 12/2012 | Sand et al. |

FOREIGN PATENT DOCUMENTS

| | | |
|---|---|---|
| EP | 284922 A2 | 10/1988 |
| EP | 491983 A1 | 7/1992 |
| EP | 557409 A1 | 9/1993 |
| EP | 649447 A1 | 4/1995 |
| EP | 679377 A2 | 11/1995 |
| EP | 757545 A1 | 2/1997 |
| EP | 796603 A1 | 9/1997 |
| EP | 991404 A1 | 4/2000 |
| EP | 1044618 A1 | 10/2000 |
| EP | 1056364 A1 | 12/2000 |
| EP | 1113768 A1 | 7/2001 |
| EP | 891160 B1 | 10/2001 |
| EP | 679377 B1 | 8/2002 |
| EP | 1287787 A1 | 3/2003 |
| EP | 995364 B1 | 6/2003 |
| EP | 1307116 B1 | 5/2005 |
| EP | 1531741 A1 | 5/2005 |
| EP | 1618806 A1 | 1/2006 |
| EP | 1691830 A1 | 8/2006 |
| EP | 1715888 A2 | 11/2006 |
| EP | 1464281 B1 | 12/2006 |
| EP | 1446028 B1 | 1/2007 |
| EP | 1772123 A1 | 4/2007 |
| EP | 1 792 577 A1 | 6/2007 |
| EP | 1800555 A1 | 6/2007 |
| EP | 1806062 A1 | 7/2007 |
| EP | 1513561 B1 | 9/2007 |
| EP | 1836981 A2 | 9/2007 |
| EP | 2007229378 A | 9/2007 |
| EP | 1885309 A2 | 2/2008 |
| EP | 1913831 A1 | 4/2008 |
| EP | 1927322 A1 | 6/2008 |
| EP | 1587506 B1 | 7/2008 |
| EP | 1952776 A1 | 8/2008 |
| FR | 2 893 496 A1 | 5/2007 |
| FR | 2 916 954 A1 | 12/2008 |
| GB | 2023404 A | 1/1980 |
| GB | 2228202 A | 8/1990 |
| GB | 2 269 753 A | 2/1994 |
| GB | 2337446 A | 11/1999 |
| GB | 2425961 A | 11/2006 |
| JP | 2071704 A | 3/1990 |
| JP | 2295572 A | 12/1990 |
| JP | 3188849 A | 8/1991 |
| JP | 4108401 A | 4/1992 |
| JP | 4129550 A | 4/1992 |
| JP | 5329005 A | 12/1993 |
| JP | 6054702 A | 3/1994 |
| JP | 6054872 A | 3/1994 |
| JP | 6062906 A | 3/1994 |
| JP | 6105859 A | 4/1994 |
| JP | 7031503 A | 2/1995 |
| JP | 7039559 A | 2/1995 |
| JP | 7241307 A | 9/1995 |
| JP | 7255763 A | 10/1995 |
| JP | 7308334 A | 11/1995 |
| JP | 7323039 A | 12/1995 |
| JP | 7324202 A | 12/1995 |
| JP | 8131477 A | 5/1996 |
| JP | 8150162 A | 6/1996 |
| JP | 8154959 A | 6/1996 |
| JP | 8243119 A | 9/1996 |
| JP | 8299016 A | 11/1996 |
| JP | 9010005 A | 1/1997 |
| JP | 9010008 A | 1/1997 |
| JP | 9028409 A | 2/1997 |
| JP | 9051801 A | 2/1997 |
| JP | 9075102 A | 3/1997 |
| JP | 9140405 A | 6/1997 |
| JP | 9191904 A | 7/1997 |
| JP | 9215501 A | 8/1997 |
| JP | 9276308 A | 10/1997 |
| JP | 9313207 A | 12/1997 |
| JP | 10043224 A | 2/1998 |
| JP | 10052472 A | 2/1998 |
| JP | 10155505 A | 6/1998 |
| JP | 10155507 A | 6/1998 |
| JP | 10155509 A | 6/1998 |
| JP | 10155512 A | 6/1998 |
| JP | 10168608 A | 6/1998 |
| JP | 10234759 A | 9/1998 |
| JP | 10328219 A | 12/1998 |
| JP | 11012803 A | 1/1999 |
| JP | 11032805 A | 2/1999 |
| JP | 11056408 A | 3/1999 |
| JP | 11076283 A | 3/1999 |
| JP | 11146802 A | 6/1999 |
| JP | 11169201 A | 6/1999 |
| JP | 11192103 A | 7/1999 |
| JP | 11276203 A | 10/1999 |
| JP | 11276208 A | 10/1999 |
| JP | 11279803 A | 10/1999 |
| JP | 11315401 A | 11/1999 |
| JP | 11318511 A | 11/1999 |
| JP | 2000060934 A | 2/2000 |
| JP | 2000093486 A | 4/2000 |
| JP | 2000116686 A | 4/2000 |
| JP | 2000116696 A | 4/2000 |
| JP | 2000116698 A | 4/2000 |
| JP | 2000232901 A | 8/2000 |
| JP | 2000287705 A | 10/2000 |
| JP | 2000308654 A | 11/2000 |
| JP | 2000316603 A | 11/2000 |
| JP | 2000325376 A | 11/2000 |
| JP | 2000328304 A | 11/2000 |
| JP | 2001000463 A | 1/2001 |
| JP | 2001029374 A | 2/2001 |
| JP | 2001087297 A | 4/2001 |
| JP | 2001095828 A | 4/2001 |
| JP | 2001104008 A | 4/2001 |
| JP | 2001140102 A | 5/2001 |
| JP | 2001269367 A | 10/2001 |
| JP | 2001299404 A | 10/2001 |
| JP | 2001299792 A | 10/2001 |

(56) References Cited

FOREIGN PATENT DOCUMENTS

| | | |
|---|---|---|
| JP | 2001353005 A | 12/2001 |
| JP | 2001355155 A | 12/2001 |
| JP | 2002000302 A | 1/2002 |
| JP | 2002052034 A | 2/2002 |
| JP | 2002065712 A | 3/2002 |
| JP | 2002165611 A | 6/2002 |
| JP | 2002209610 A | 7/2002 |
| JP | 2002209931 A | 7/2002 |
| JP | 2002282011 A | 10/2002 |
| JP | 2002345501 A | 12/2002 |
| JP | 2002355105 A | 12/2002 |
| JP | 2003000629 A | 1/2003 |
| JP | 2003033204 A | 2/2003 |
| JP | 2003052728 A | 2/2003 |
| JP | 2003126130 A | 5/2003 |
| JP | 2003210206 A | 7/2003 |
| JP | 2003250601 A | 9/2003 |
| JP | 2003319804 A | 11/2003 |
| JP | 2004166810 A | 6/2004 |
| JP | 2004167069 A | 6/2004 |
| JP | 2004167144 A | 6/2004 |
| JP | 2004180746 A | 7/2004 |
| JP | 2004201933 A | 7/2004 |
| JP | 2004202074 A | 7/2004 |
| JP | 2004202128 A | 7/2004 |
| JP | 2004215870 A | 8/2004 |
| JP | 2004216087 A | 8/2004 |
| JP | 2004229992 A | 8/2004 |
| JP | 2004242988 A | 9/2004 |
| JP | 2004250796 A | 9/2004 |
| JP | 2004329452 A | 11/2004 |
| JP | 2005000347 A | 1/2005 |
| JP | 2005009011 A | 1/2005 |
| JP | 2005013682 A | 1/2005 |
| JP | 2005021191 A | 1/2005 |
| JP | 2005040571 A | 2/2005 |
| JP | 2005042213 A | 2/2005 |
| JP | 2005052593 A | 3/2005 |
| JP | 2005152218 A | 6/2005 |
| JP | 2005160560 A | 6/2005 |
| JP | 2005245471 A | 9/2005 |
| JP | 2005245571 A | 9/2005 |
| JP | 2005279188 A | 10/2005 |
| JP | 2005281917 A | 10/2005 |
| JP | 2005287726 A | 10/2005 |
| JP | 2005305063 A | 11/2005 |
| JP | 2005305085 A | 11/2005 |
| JP | 2005349225 A | 12/2005 |
| JP | 2006000403 A | 1/2006 |
| JP | 2006000549 A | 1/2006 |
| JP | 2006043369 A | 2/2006 |
| JP | 2006043376 A | 2/2006 |
| JP | 2006055591 A | 3/2006 |
| JP | 2006081797 A | 3/2006 |
| JP | 2006130248 A | 5/2006 |
| JP | 2006132037 A | 5/2006 |
| JP | 2006141651 A | 6/2006 |
| JP | 2006187545 A | 7/2006 |
| JP | 2006247335 A | 9/2006 |
| JP | 2006249623 A | 9/2006 |
| JP | 2006263407 A | 10/2006 |
| JP | 2006271915 A | 10/2006 |
| JP | 2006288491 A | 10/2006 |
| JP | 2006289003 A | 10/2006 |
| JP | 2006314656 A | 11/2006 |
| JP | 2006326264 A | 12/2006 |
| JP | 2007090017 A | 4/2007 |
| JP | 2007097846 A | 4/2007 |
| JP | 2007130369 A | 5/2007 |
| JP | 2007167180 A | 7/2007 |
| JP | 2007215967 A | 8/2007 |
| JP | 2007236905 A | 9/2007 |
| JP | 2007244786 A | 9/2007 |
| JP | 2007252585 A | 10/2007 |
| JP | 2007313043 A | 12/2007 |
| JP | 2007319201 A | 12/2007 |
| JP | 2007330743 A | 12/2007 |
| JP | 2008000244 A | 1/2008 |
| JP | 2008023258 A | 2/2008 |
| JP | 2008023300 A | 2/2008 |
| JP | 2008061960 A | 3/2008 |
| JP | 2008093399 A | 4/2008 |
| JP | 2008121177 A | 5/2008 |
| WO | WO8504558 A1 | 10/1985 |
| WO | WO8901745 A1 | 3/1989 |
| WO | WO9211777 A1 | 7/1992 |
| WO | WO9401496 A1 | 1/1994 |
| WO | WO9528887 A1 | 11/1995 |
| WO | WO9629988 A1 | 10/1996 |
| WO | WO9641523 A1 | 12/1996 |
| WO | WO9721404 A1 | 6/1997 |
| WO | WO9735528 A1 | 10/1997 |
| WO | WO9858631 A1 | 12/1998 |
| WO | WO9943227 A1 | 9/1999 |
| WO | WO0006036 A1 | 2/2000 |
| WO | WO0015163 A1 | 3/2000 |
| WO | WO 00/18313 | 4/2000 |
| WO | WO0121119 A1 | 3/2001 |
| WO | WO0191674 A1 | 12/2001 |
| WO | WO0211573 A1 | 2/2002 |
| WO | WO0217840 A1 | 3/2002 |
| WO | WO0241944 A2 | 5/2002 |
| WO | WO02098254 A1 | 12/2002 |
| WO | WO03045179 A2 | 6/2003 |
| WO | WO03099144 A1 | 12/2003 |
| WO | WO03099344 A2 | 12/2003 |
| WO | WO2004056305 A2 | 7/2004 |
| WO | WO2004058286 A1 | 7/2004 |
| WO | WO2004069866 A1 | 8/2004 |
| WO | WO2004078220 A2 | 9/2004 |
| WO | WO2004107895 A1 | 12/2004 |
| WO | WO2005013745 A1 | 2/2005 |
| WO | WO2005034670 A2 | 4/2005 |
| WO | WO2005039439 A2 | 5/2005 |
| WO | WO2005056050 A1 | 6/2005 |
| WO | WO2005079828 A2 | 9/2005 |
| WO | WO2005102092 A1 | 11/2005 |
| WO | WO2006030546 A1 | 3/2006 |
| WO | WO2006047227 A1 | 5/2006 |
| WO | WO2006058140 A2 | 6/2006 |
| WO | WO2006066419 A1 | 6/2006 |
| WO | WO2006069451 A1 | 7/2006 |
| WO | WO2006069452 A1 | 7/2006 |
| WO | WO2006088412 A1 | 8/2006 |
| WO | WO2006107779 A2 | 10/2006 |
| WO | WO2006120385 A2 | 11/2006 |
| WO | WO2007008348 A2 | 1/2007 |
| WO | WO2007021865 A2 | 2/2007 |
| WO | WO2007025520 A1 | 3/2007 |
| WO | WO2007089617 A2 | 8/2007 |
| WO | WO2007098057 A2 | 8/2007 |
| WO | WO2007106498 A2 | 9/2007 |
| WO | WO2008006929 A1 | 1/2008 |
| WO | WO2008102405 A1 | 8/2008 |
| WO | WO2008118426 A1 | 10/2008 |
| WO | WO 2009/018527 | 2/2009 |
| WO | WO 2010/093696 | 8/2010 |

OTHER PUBLICATIONS

H. Kelikian, M.D., "Miscellaneous Methods", Hallux Valgus, Allied Deformities of the Forefoot and Metatarsalgia, 1965, pp. 253-261, W.B. Saunders Company, Philadelphia and London.
International Search Report and Written Opinion issued in PCT/US2010/049583, mailed Dec. 10, 2010, 13 pages.
International Search Report and Written Opinion issued in PCT/US2011/039041, mailed Oct. 19, 2011, 14 pages.
Coughlin et al., "Proximal metatarsal osteotomy and distal soft tissue reconstruction as treatment for hallux valgus deformity", Keio J. Med. 54(2) p. 60-65, 2005.
RetroButton™ ACL Reconstruction, Arthrex® 8 pages, © Copyright Arthrex Inc., 2007.
Mini TightRope® Surgical Technique, © Copyright 2007, 6 pages.

* cited by examiner

METHODS AND DEVICES FOR TREATING HALLUX VALGUS

FIELD OF THE INVENTION

The various embodiments disclosed herein relate to methods and devices for treating hallux valgus. More specifically, certain embodiments relate to devices having anchors and a dynamic tightening system to correct joint deformity.

BACKGROUND OF THE INVENTION

Hallux valgus deformities in the human foot typically relate to at least one of two conditions: a deviated position of the great toe where the great toe leans in towards the second toe, and a deviation in the angle between the first and second metatarsal bones of the foot. The most commonly used medical terms associated with these deformities are "hallux valgus" and "hallux abducto valgus," where "hallux" refers to the great toe, "valgus" refers to the abnormal slant of the great toe, and "abducto" refers to the abnormal slant or leaning of the great toe towards the second toe, as shown in FIGS. 1A and 1B.

There are generally four stages in the development of hallux abducto valgus ("HAV"). Stage one involves a lateral shift of the entire hallux upon the first metatarsal head. Stage two relates to abduction of the hallux. In stage three, because abduction of the hallux displaces the long flexor and extensor tendons laterally, contraction of these muscles during the propulsive period produces a retrograde medially directed component of force as the proximal phalanx pushes the first metatarsal in an adducted position. Finally, stage four involves complete dislocation of the first MPJ, which rarely occurs without underlying rheumatic inflammatory disease or neuromuscular disorder. In some situations, HAV may lead to the formation of a bunion. "Bunion" refers to the pathological bump, callous, and/or inflammation on the side of the great toe joint associated with either a bursal sac or a bone deformity.

The abnormalities associated with development of hallux valgus as described above are caused by a biomechanical abnormality, where certain tendons, ligaments, and supportive structures of the first metatarsal are no longer functioning correctly. While the underlying mechanisms are not fully understood, this biomechanical abnormality may be due to the structure of the foot (such as flat feet, excessive ligamentous flexibility, or abnormal bone structure), certain neurological conditions, poor-fitting footwear, or just chronic "wear and tear" leading to a progression of initially small irregularities.

Various treatments for hallux valgus and/or bunions exist. Various surgical procedures may address some combination of removing the abnormal bony enlargement of the first metatarsal, realigning the first metatarsal relative to the adjacent metatarsal, straightening the great toe relative to the first metatarsal and adjacent toes, realigning the cartilagenous surfaces of the great toe joint, repositioning the sesamoid bones beneath the first metatarsal, and correcting any abnormal bowing or misalignment within the great toe. Further treatments can include bunion pads and external splints. All of these known treatments have shortcomings in either effectiveness (pads and splints) or invasiveness (the surgical procedures). With respect to the existing surgical procedures, the vast majority require an osteotomy which leads to long recovery and the need for patients to wear a cast or surgical boot for weeks following the operation. Further, the surgical patients are left with a significant scar and poor cosmesis. In addition, studies have highlighted that as many as 30% of bunion surgery patients are unhappy with the result and nearly 10% have post-surgical complications. Finally, the surgical procedures are costly, requiring anesthesia, a lengthy operating time, and multiple trained medical staff.

BRIEF SUMMARY OF THE INVENTION

One embodiment disclosed herein relates to an implantable tensioning device. The device has a first anchor, a dynamic tension component coupled to the first anchor, and a second anchor coupled to the dynamic tension component. The first anchor is configured to be attachable to a first metatarsal bone and the second anchor is configured to be attachable to a second metatarsal bone. The dynamic tension component exhibits elasticity and has a tensioned state and an untensioned state. The tensioned state includes the component urging the first and second anchors toward each other. In certain implementations, the dynamic tension component has elastic material. In other implementations, the dynamic tension component is a spring. According to certain embodiments, the length of the dynamic tension component in the tensioned state is at least 10% greater than a length of the dynamic tension component in the untensioned state.

Another embodiment relates to a method of treating a bone deformity. The method includes securing a first anchor to a first metatarsal bone, securing a second anchor to a second metatarsal bone, securing a dynamic tension component to the first and second anchors such that the dynamic tension component is in a tensioned state, and urging the first and second metatarsal bones toward each other with the dynamic tension component. In this embodiment, the dynamic tension component exhibits elasticity and moves toward an untensioned state as the first and second metatarsal bones move toward each other.

A further embodiment relates to another method of treating a bone deformity. The method includes providing an implant device having a first anchor, a dynamic tension component coupled to the first anchor, and a second anchor coupled to the dynamic tension component. The dynamic tension component includes heat shrink material. The method further includes securing the first anchor of the device to a first metatarsal bone, securing the second anchor of the device to a second metatarsal bone, and applying heat to the dynamic tension component, whereby the dynamic tension component shrinks into a first tensioned state. In addition, the method includes urging the first and second metatarsal bones toward each other with the dynamic tension component, wherein the dynamic tension component moves toward a first untensioned state as the first and second metatarsal bones move toward each other.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Various embodiments disclosed herein relate to methods and devices for treating hallux valgus (bunions). More specifically, various embodiments herein relate to dynamic tightening or connection systems that couple at least the first and second metatarsals. Certain implementations apply a dynamic tightening force that urges the first and second metatarsals together, thereby providing a slow correction of the joint deformity by decreasing the metatarsal angle over time without requiring the acute damage to the bones or tendons of the foot such as that created by an osteotomy. A device that applies a "dynamic tightening force" is a device that allows for the first metatarsal to be repositioned toward its normal (non-deviated) position while continuing to apply a corrective force as the first metatarsal moves toward a corrected position. That is, a "dynamic tension component" or "dynamic tension mechanism" as described herein is a component or mechanism that allows for gradual movement of the first metatarsal while continuing to apply a corrective force to that bone. As such, various embodiments disclosed herein provide treatment of hallux valgus with reduced trauma and quicker recovery in comparison to known systems and treatments. While some embodiments provide a non-adjustable tightening force, others provide an adjustable or controllable tightening force.

Figure 1A:
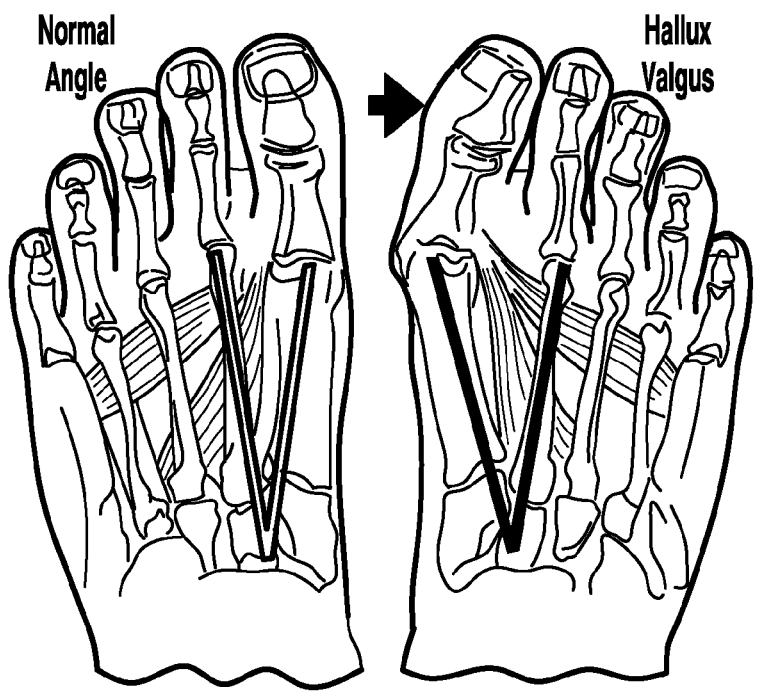
FIG. 1A is a schematic depiction of a healthy foot and a foot exhibiting hallux valgus.
Figure 1B:
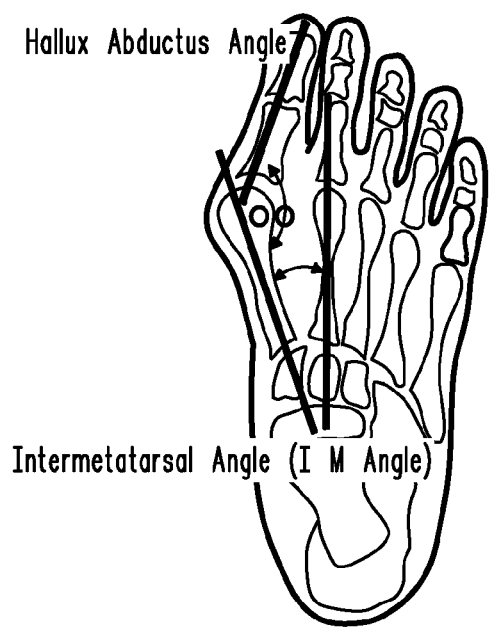
FIG. 1B is a schematic depiction of a second foot exhibiting hallux valgus.
Figure 2:
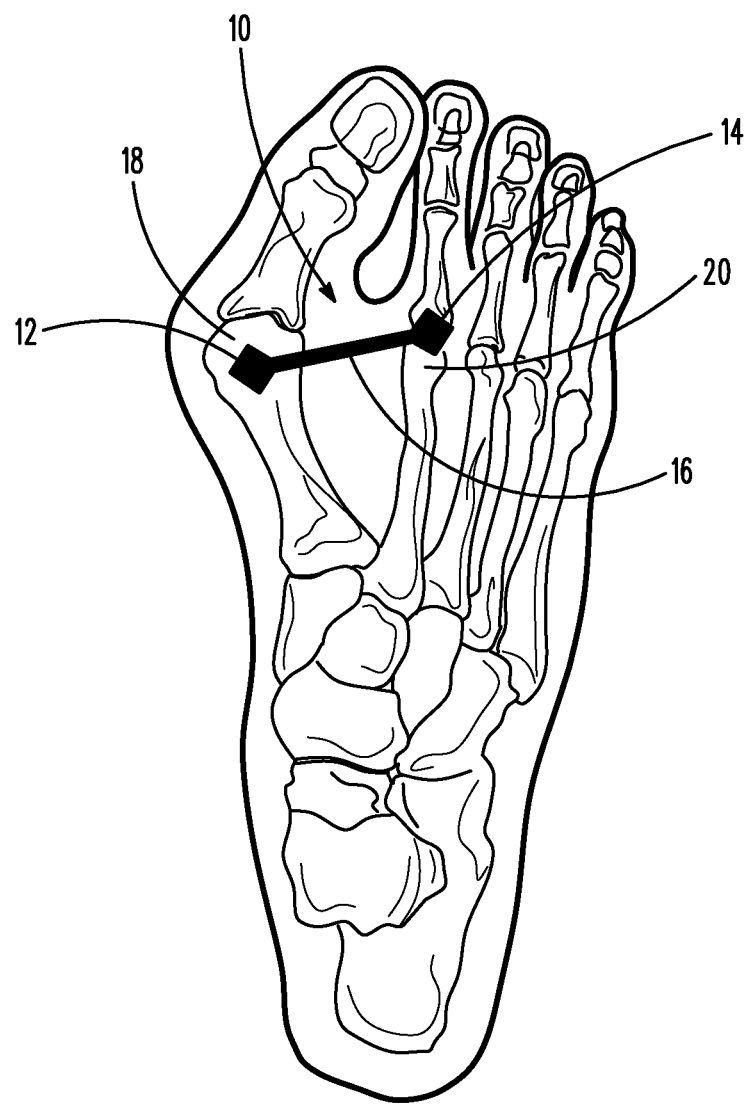
FIG. 2 is a schematic depiction of an implantable bone deformity treatment device in a foot exhibiting hallux valgus, according to one embodiment.

FIG. 2 provides a schematic depiction of certain devices and systems described herein, according to one embodiment. In this figure, the device 10 is an implant that is coupled at a first anchor 12 to the first metatarsal 18 and at a second anchor 14 to the second metatarsal 20. The anchors 12, 14 can take a variety of forms, including several discussed below. In addition, the device 10 has a tension or flexibility component 16, as will be described in further detail herein. It is understood that each of the various device and method embodiments disclosed herein can be the sole treatment for the bone deformity. It is further understood that any of these embodiments could also be used in conjunction with any one or more of other known treatments, such as surgical repositioning of the bones, surgical removal of the underlying bunion, pads, splints, or any other treatment method or device.

In certain embodiments, the tension or flexibility component 16 exhibits elasticity. "Elasticity" is the physical property of a material that deforms under stress (e.g. external forces), but returns to its original shape when the stress is removed. The amount of deformation is called the strain. As an example, many versions of the dynamic tension components made of elastic material and those configured as springs have elasticity as defined herein. That is, each of these components can be urged into a deformed or strained configuration and then, as a result of the component's elasticity, will apply a force as the component returns to its original shape.

Figure 3A:
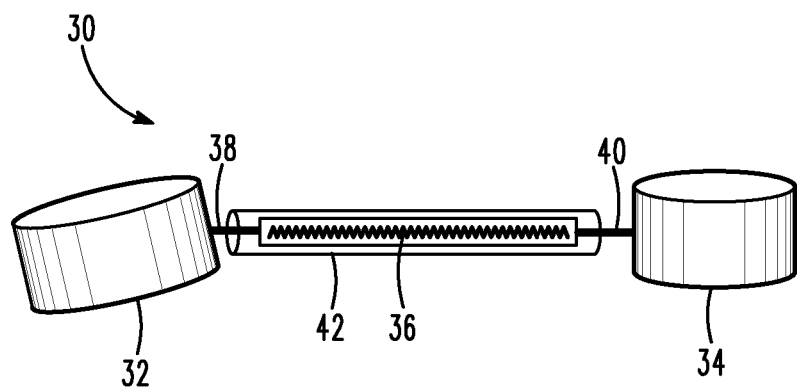
FIG. 3A is a front view of an implantable tensioning device, according to one embodiment.

FIG. 3A depicts a device 30 including elastic material, according to one embodiment. In this embodiment, the device 30 includes a first anchor 32, a second anchor 34, and an elastic dynamic tension component 36. As shown, the anchors 32, 34 are sleeves or straps adapted to surround the appropriate metatarsal. In other embodiments, the anchors have alternative configurations as further discussed below. The elastic tension component 36 is configured to apply a force urging the first anchor 32 and second anchor 34 toward each other as the component 36 returns from its tensioned state (in which it has been deformed) to its untensioned state or original shape, as described above. In addition, the device 30 has a first connecting component 38 coupling the elastic component 36 to the first anchor 32 and a second connecting component 40 that couples the elastic component 36 to the second anchor 34, along with an enclosure or housing 42 that surrounds or encloses the elastic component 36. Alternatively, the elastic component 36 can be coupled directly to the two anchors 32, 34. In certain additional alternative embodiments, there is no enclosure.

In one embodiment, the elastic component 36 is configured to have an untensioned (or original) length that is less than the distance between the two connecting components 38, 40 when the device 30 is coupled at the first and second anchors 32, 34 to the patient's first and second metatarsals. That is, the elastic component 36 is configured to be tensioned (or deformed) when the device is surgically positioned on the patient's foot such that the component 36 applies a force pulling the two metatarsals together and continues to apply that force even as the two metatarsals get closer together. In addition, the elastic component 36 may be further configured such that as the two metatarsals are slowly pulled together over time—thereby treating the hallux valgus—the elastic component 36 reaches its untensioned length when the first metatarsal is urged inward so far that the hallux valgus is fully or at least partly treated or corrected. Alternatively, the elastic component 36 may be configured such that its untensioned length is not reached when the hallux valgus is fully treated. For example, the elastic component 36 may be configured to remain in a tensioned state even after the hallux valgus has been fully treated in order to maintain the first metatarsal in the correct position in relation to the second metatarsal. It is understood that, according to certain embodiments, the force decreases as the first metatarsal moves toward the second metatarsal.

According to one implementation, the elastic component 36 is configured such that the change from the tensioned length to the untensioned length constitutes a change of at least 10% from the tensioned length. Alternatively, the change from the tensioned to the untensioned length constitutes a change of at least 25% in the length. In a further embodiment, the amount of change constitutes a change of at least 50%.

Figure 3B:
FIG. 3B is a front view of an elastic dynamic tensioning component, according to one embodiment.

In certain versions, the elastic component 36 is comprised of silicone rubber. Alternatively, the elastic component can be made of one of or a combination of two or more of silicone rubber, PEBA such as Pebax™, polyurethane, latex, or any other elastomeric materials that can be used in such implant devices as those describe herein. In another alternative, as shown schematically in FIG. 3B, an elastic component 44 is contemplated that is made of a commercially available elastic material such as Lycra™ or Nylon™. In yet a further alternative embodiment, the elastic component is made of any known elastic material that could be used in a device as described herein.

In one implementation, the elastic component 36 is structured as a monofilament component. Alternatively, the component 36 is a multifilament component. In a further embodiment, the component 36 is a braided multifilament component.

Figure 4A:
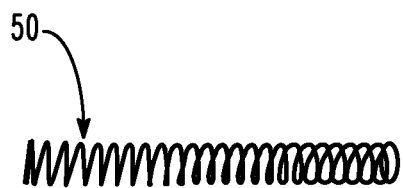
FIG. 4A is a front view of a spring, according to one embodiment.
Figure 4B:
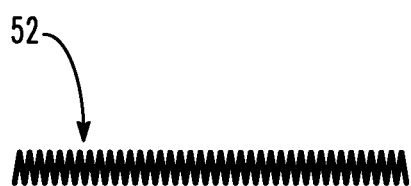
FIG. 4B is a front view of a spring, according to another embodiment.

FIGS. 4A and 4B depicts alternative embodiments in which the dynamic tension component is a spring. More specifically, FIG. 4A depicts a tensioned spring 60, while FIG. 4B depicts a heat-activated spring 70.

Turning first to the tensioned spring 60 of FIG. 4A, the spring 60 is made of stainless steel. In alternative implementations, the spring can be made of superelastic material or a shape memory alloy (such as nitinol, for example). For example, the spring 60 is made of any of stainless steel, titanium, tungsten, or a chromium cobalt alloy such as MP35N. In a further alternative, the spring 60 is made of any known material that can be used in a tensioned spring for a device as described herein. In one embodiment, like the elastic component 38 described above, the spring 60 is configured to be under tension when the device (not shown) is positioned in the patient's foot such that the spring 60 applies a force that urges the first and second metatarsals together.

Turning now to the heat-activated spring 70 of FIG. 4B, the spring 70 is made of shape-memory or heat-activated nitinol. Alternatively, the spring 70 can be made of a heat-activated polymer. Regardless of the material, the spring 70 is heat-activated such that the application of heat causes the spring 70 to shorten in length, thereby increasing the force applied to urge the first and second metatarsals together. In this embodiment, the spring 70 can be positioned in a device (such as any of the devices discussed herein) such that the spring shortens and thus applies a predetermined amount of tensile force urging the two metatarsals together. Then, in this embodiment, as the applied force causes the first metatarsal to move toward the second (thereby treating, partially or completely, the hallux valgus), and the force applied by the spring lessens as a result, heat can be applied to shorten the length of the spring 70 and thereby increase the tension and the amount of force being applied.

Alternatively, the spring 70 and the device can be positioned such that the spring 70 is NOT tensioned, and then after the device is positioned, the heat can be applied to "activate" the spring 70 by causing the spring to shorten in length and thereby create tension such that a force is applied urging the two metatarsals together.

In a further embodiment, the heat required to activate the spring 70 could be the body heat of the patient, and thus, the spring 70 would be configured to provide increasing force over time. That is, the body heat of the patient would cause the spring 70 to begin to shorten soon after the spring 70 and the overall device (not shown) is implanted, thereby providing an increase in the tightening force over time. Such dynamic tightening would reduce or eliminate the possibility of the first metatarsal moving toward the second metatarsal so far that the spring is no longer tensioned without the hallux valgus being fully treated.

Figure 5:
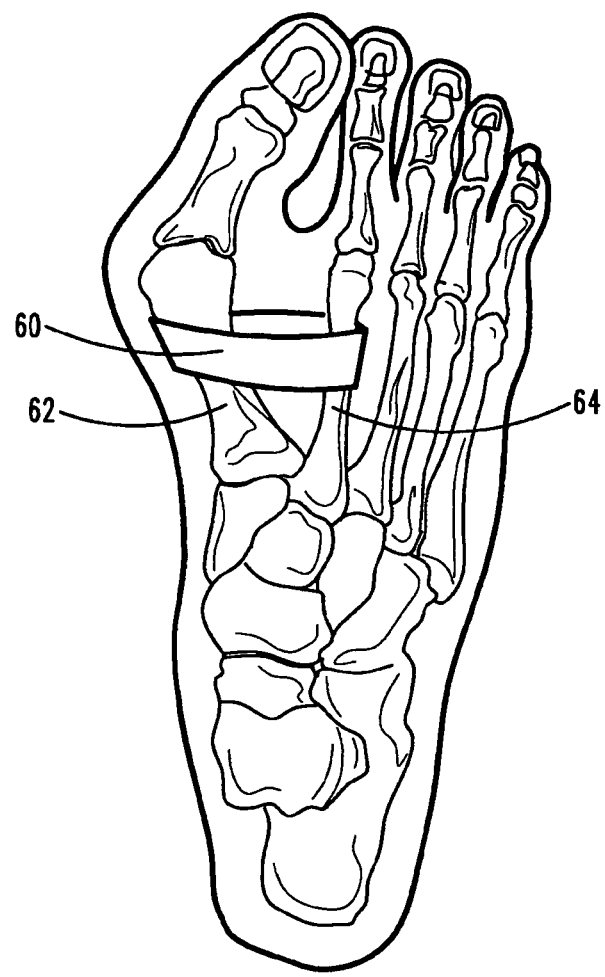
FIG. 5 is a schematic depiction of another implantable bone deformity treatment device in a foot exhibiting hallux valgus, according to one embodiment.

FIG. 5 depicts another embodiment of a treatment device 60 consisting of an elastic band 60 that can be positioned around both the first 62 and second 64 metatarsals. Like the device 30 depicted in FIG. 3, this device 60 has an elastic dynamic tension component, which in this implementation is the band 60 itself.

In one embodiment, the band 60 is configured to have an untensioned length that is less than the distance between the first 62 and second metatarsals 64 such that the device 60 is tensioned when it is implanted. In a further implementation, the band 60 can be configured such that it reaches its untensioned length when the first metatarsal 62 is urged inward to the point that the hallux valgus is fully or at least partially treated or corrected. Alternatively, the band 60 can be configured such that its untensioned length is not reached when the hallux valgus is fully corrected.

The band 60, according to one embodiment, can consist of single, non-looped piece of elastic material that is first surgically positioned around the first and second metatarsals 62, 64 and then the two ends of the piece are attached to each other to form the band 60. Alternatively, the band 60 could initially consist of two or more pieces of elastic material that are first positioned around the metatarsals 62, 64 and then attached to each other to form the band 60.

According to one embodiment, the band 60 is positioned around the two metatarsals 62, 64 such that no anchor or attachment component of any kind is required. Alternatively, the band 60 can be positioned around the metatarsals 62, 64 and then attached to each metatarsal by tacks or other kinds of anchors such as those described herein.

In an alternative implementation, the band 60 is made of a "heat shrink" material such as, for example, a cross-linked polyolefin heat shrink in which the band 60 is coated or impregnated with an material such as metallic powder that can be heated inductively. Alternatively, the heat shrink material can be cross-linked PTFE. In a further embodiment, the heat shrink material can be any known material that can be shrunk, shortened, or otherwise reduced in size by the application of heat. In such an embodiment, the band 60 can initially be configured to have an untensioned length that is the same as or greater than the distance between the first 62 and second metatarsals 64 such that the device 60 is untensioned when it is implanted. Once the band 60 is positioned correctly, heat can be applied to the band 60 such that the band 60 begins to shrink, thereby decreasing the untensioned length and resulting in a force being applied to the first metatarsal 62 urging it toward the second 64. Further heat can be applied over time to further shrink the band 60 and thus further decrease the untensioned length and result in further force being applied.

In one version, the heat energy that is applied to the heat shrink band 60 is RF energy. Alternatively, any known heat source capable of shrinking the heat shrink band 60 can be used. Further, it is understood that the heat can be applied regularly, such as daily, weekly, monthly, or at any other intervals. Alternatively, the heat can be applied as needed, such that the heat is only applied when the first metatarsal 62 has moved some predetermined distance toward the second metatarsal 64.

Figure 6:
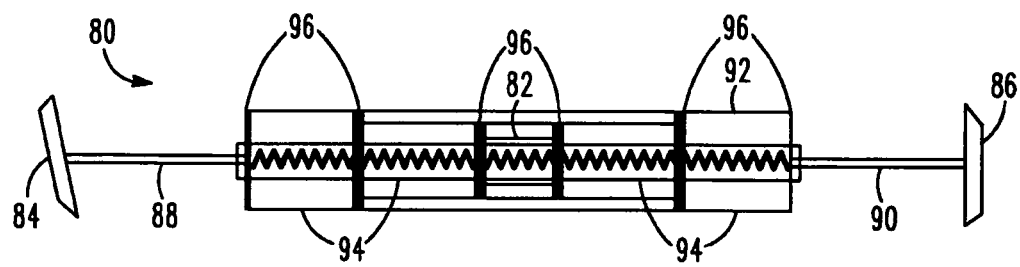
FIG. 6 is a front view of a controllable or adjustable tensioning device, according to one embodiment.

Other embodiments provide controllable or adjustable dynamic tension or tightening, such as the embodiment depicted in FIG. 6. In this implementation, the device 80 has a first anchor 84, second anchor 86, a dynamic tension component 82, a first connection component 88 coupled to the first anchor 84, and a second connection component 90 coupled to the second anchor 86. Alternatively, the tension component 82 is coupled directly to the first and second anchors 84, 86. The device 80 also has a housing 92 that houses the tension component 82 and four bioabsorbable components 94 disposed between support components 96.

While FIG. 6 depicts four bioabsorbable components 94, the number of components can range from one to any number of such components depending on the device and the patient's foot. In one embodiment in which the patient's hallux valgus is a severe case, the device has more than four bioabsorbable components 94. In an alternative embodiment in which the patient has a mild case of hallux valgus, the device has less than four bioabsorbable components 94. It is understood that the number of components is determined by far more variables than just the severity of the condition, including the size of the patient's foot, the size of the components 94, and various other variables.

The bioabsorbable components 94 can be any such known components. In one example, the bioabsorbable components can be made with one or more of the bioabsorbable products available from Tepha Inc., of Lexington, Mass., which are polyhydroxyalkanoates or naturally occurring thermoplastic polyester biomaterials with structures that resemble existing synthetic absorbable biomaterials. Alternatively, the components 94 can be degradable components 94 made of a known degradable material such as poly-lactic acid or poly-glycolic acid.

The support components 96 can be any components that can be positioned on either side of the bioabsorbable components 94 to provide structure to the housing 92 and further to help maintain the tensioned state of the tension component 82 as described in further detail below. According to one embodiment, the outermost two support components 96 are coupled to the tension component 82 such that the two components 96—along with the bioabsorbable components 94—maintain the tensioned state of the tension component 82. In one implementation, the support components 96 are made of a bioabsorbable material. Alternatively, the support components can be made of stainless steel or any other rigid, substantially rigid, or solid material that can be used in medical implants.

The bioabsorbable components 94 provide for some control or adjustability with respect to the tension component 82. In one version, the device 80 is implanted or positioned in the patient's foot in a manner similar to those embodiments described above: the first and second anchors 84, 86 are anchored to the first and second metatarsals, respectively. The dynamic tension component 82 is configured to be under tension when the device 80 is properly positioned, but unlike some of the prior embodiments, the tension component 82 in this embodiment is under tension at least in part because of the bioabsorbable components 94. That is, the bioabsorbable components 94 are configured to be positioned so as to maintain the tensioned state of the tension component 82. More specifically, according to one implementation, the bioabsorbable components 94 are positioned to maintain the length of the tension component 82—such that it is held in a tensioned state—by serving as physical spacers between the support components 96.

In one embodiment, the device 80 is implanted or positioned such that the dynamic tension component 82 applies a force that urges the first and second metatarsals together. In this embodiment, the force applied to the two metatarsals causes the first metatarsal to move toward the second metatarsal over time, thereby treating the hallux valgus. As the first metatarsal moves toward the second, the length of the tension component 82 decreases and thus the applied force decreases as the length of the tension component 82 reaches the minimum allowed length as determined by the yet-to-be absorbed bioabsorbable components 94 and the support components 96. However, at the same time, the bioabsorbable components 94 are slowly being absorbed and thus are decreasing in size. As the components 94 decrease in size, the support components 96 move closer together and thus can no longer maintain the same length of the tension component 82, thereby allowing the tension component 82 to shorten and thereby apply a greater force urging the first metatarsal toward the second than if the components 94 were not being absorbed.

This absorption of the bioabsorbable components 94 provides for a controlled contraction of the overall device. Thus, the amount of bioabsorbable material in each well or disposed in each space between the support components 96 determines the amount of time required for the device to contract. The more material in the wells or spaces, the longer it takes for the device to contract and thus the more time required to apply the corrective force to the first and second metatarsals. In addition, the formulation or the type of bioabsorbable material can also influence the amount of time required for the material to absorb and thus for the device to contract. In one embodiment, the formulation or material of every bioabsorbable component 94 can be chosen to absorb at a specific predetermined rate. Alternatively, the various bioabsorbable components 94 in the device 80 can have different predetermined rates, thereby providing for different components 94 in the same device 80 absorbing at different rates, resulting in contraction at different rates. In a further alternative, various versions of the same device 80 can be provided with different bioabsorbable components 94 having different absorption rates, thereby providing a range of devices 80 with different contraction rates over time.

According to another implementation, the contraction of the device as a result of the absorption of the bioabsorbable material can occur gradually. Alternatively, the contraction can occur in quick steps, with the absorption or partial absorption of a single bioabsorbable component 94 causing a relatively fast contraction of the device equivalent to the amount of the absorption.

In an alternative embodiment, the device 80 is implanted or positioned such that the tension component is in its untensioned state, and thus does not apply any tightening force. This embodiment may be used when it is desirable that the tightening force not be applied immediately after implantation/positioning of the device. In this implementation, the bioabsorbable components 94 begin to dissolve or be absorbed after implantation. As the components 94 decrease in size, the length of the tension component 82 decreases and force is applied urging the first metatarsal toward the second. This force increases as the components 94 decrease in size, thereby resulting in a dynamic or increasing tension over time.

In various implementations, the length, thickness, material, etc. of the bioabsorbable components 94 are selected to engineer a desired rate of increasing tension. In other words, for example, each segment is designed to be absorbed at a predetermined time, thereby releasing the tension component 82 to increase tension.

Each of the systems or devices discussed above has two anchors—one for each of the metatarsals. Various embodiments of these anchors are provided herein.

Figure 7A:
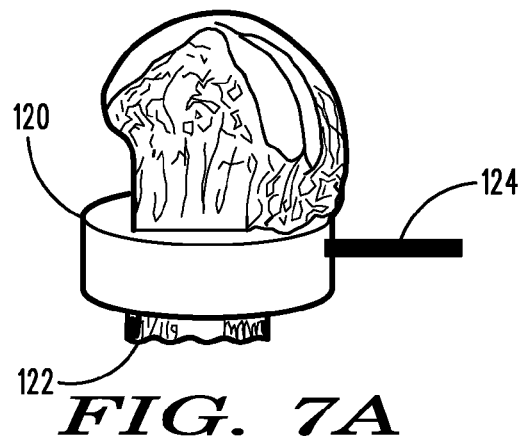
FIG. 7A is a schematic view of an anchor coupled to a bone, according to one embodiment.

FIG. 7A depicts an anchor 120 that is a sleeve configured to be wrapped or otherwise positioned around the outside of the metatarsal 122. The sleeve 120 is then coupled to the tension device 124. According to alternative implementations, the anchor 120 is a strap that is configured to be positioned around the outside of the metatarsal 122 and then coupled to the tension device 124.

Figure 7B:
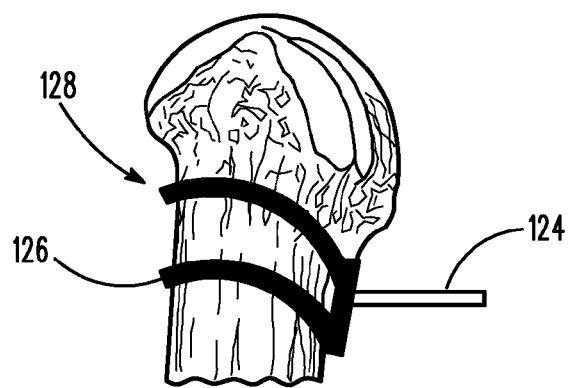
FIG. 7B is a schematic view of another anchor coupled to a bone, according to another embodiment.

FIG. 7B depicts another embodiment of an anchor 126, in which the anchor 126 is a wire or suture wrapped or otherwise positioned around the outside of the metatarsal 128, and is coupled to the body 130 of the tension device. The anchor 126 is also referred to as a "lasso." Like the sleeve 120, the lasso anchor 126 is wrapped around the bone 128 rather than being inserted through it.

Figure 7C:
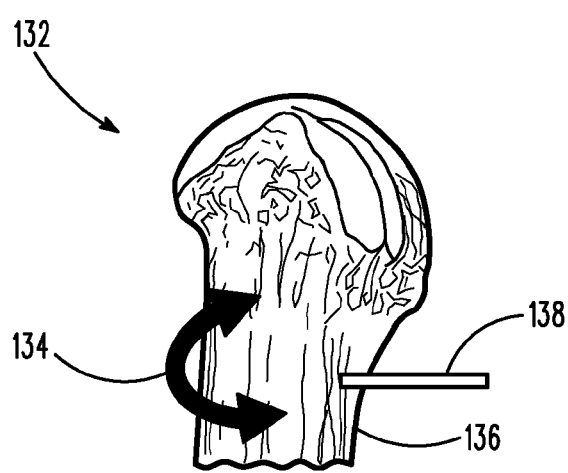
FIG. 7C is a schematic view of yet another anchor coupled to a bone, according to a further embodiment.

Another anchor embodiment is shown in FIG. 7C, which depicts an anchor 132 that is positioned entirely through the width of the metatarsal 136 and includes a body 134 positioned on one side of the metatarsal 136 while being coupled to the dynamic tension component 138 of the device on the other side. In one embodiment, the anchor 132 is inserted through the bone 136 and then the body 134 is deployed. Alternatively, the anchor 132 can be positioned by any known method.

Figure 7D:
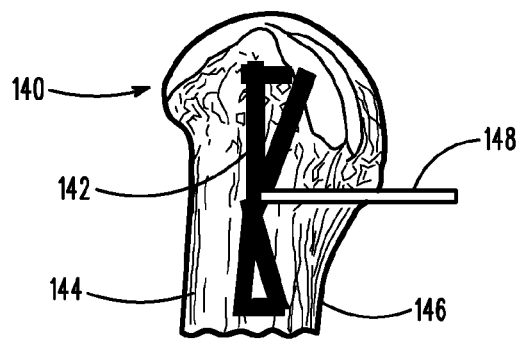
FIG. 7D is a schematic view of a further anchor coupled to a bone, according to a further embodiment.

Yet another embodiment is the intramedullary anchor 140 depicted in FIG. 7D. The intramedullary anchor 140 is not inserted entirely through the width of the metatarsal 144. Instead, the body 142 of the anchor 140 is positioned inside the intramedullary canal 146 of the bone 144 and deployed in the canal 146 such that the anchor is firmly engaged therein. One possible advantage of this configuration, according to one embodiment, is that the force of the device is not focused on an outside portion of the bone, but rather is distributed along the length of the anchor body 142 within the canal 146.

According to various implementations, the intramedullary anchor 140 is made up of a superelastic material or a shape memory alloy (such as nitinol) adapted to be delivered into the canal in a compressed state and to then expand inside the canal for anchoring.

These various anchor embodiments, such as the anchor 142 depicted in FIG. 7D for example, can be attached to the dynamic tension component in a variety of different ways. For example, according to one embodiment (using anchor 142 as an example), the anchor 142 is coupled to the dynamic tension component 148 via a hole in the anchor 142 through which the end of the tension component 148 is disposed. In this embodiment, the end of the tension component 148 that is positioned through the hole can be oversized or have a button or other type of end component attached to it such that the end component cannot pass through the hole and thus creates an interference fit with the anchor 142. Alternatively, the anchor 142 and tension component 148 can be coupled via a braid that is fitted to both the anchor 142 and tension component 148. In a further alternative, the tension component 148 can be looped around the anchor 142.

Figure 7E:
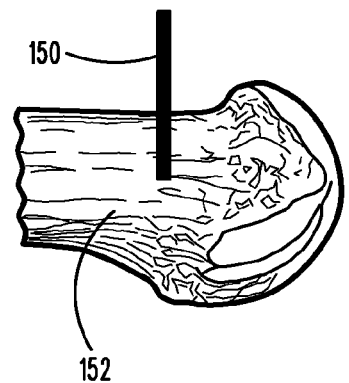
FIG. 7E is a schematic view of an anchor coupled to a bone, according to a further embodiment.

A further embodiment is the top-of-the-metatarsal anchor 150 depicted in FIG. 7E. In this embodiment, the anchor 150 is drilled into or otherwise coupled to the top of the metatarsal 152. One possible advantage of this configuration, according to one implementation, is the minimally invasive nature of inserting the anchor 150 into the top of metatarsal 152, rather than having to insert it through or wrap it around the metatarsal, as well as the added strength of this part of the metatarsal bone.

Figure 7F:
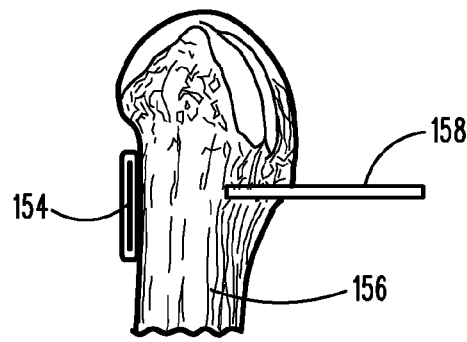
FIGS. 7F and 7G are schematic views of another anchor coupled to a bone, according to a further embodiment.
Figure 7G:

FIGS. 7F and 7G depict another implementation having an anchor that, like the anchor depicted in FIG. 7C, is positioned entirely through the width of the metatarsal 156 and includes a body 154 positioned on one side of the metatarsal 156 while being coupled to the dynamic tension component 158 of the device on the other side. In this embodiment, the body 154 is a plate 154 that can be fixated to the side of the metatarsal 156. According to certain variations, the body 154 can be pliable and further can be configured to be contoured to match the shape of the side of the metatarsal 156 to which it is attached. In one embodiment, the body 154 is inserted through the bone 156 and then deployed. Alternatively, the body 154 can be positioned by any known method.

In a further implementation, the anchor can be any button embodiment as disclosed in U.S. Published Application 2008/0208252, entitled "Bunion Repair Using Suture-Button Construct," which is hereby incorporated herein by reference in its entirety.

Various additional alternative embodiments are also contemplated herein. For example, various alternative configurations as depicted in FIGS. 8A, 8B, and 8C are designed for force distribution, thereby reducing the amount of force on any one point or bone of the foot.

Figure 8A:
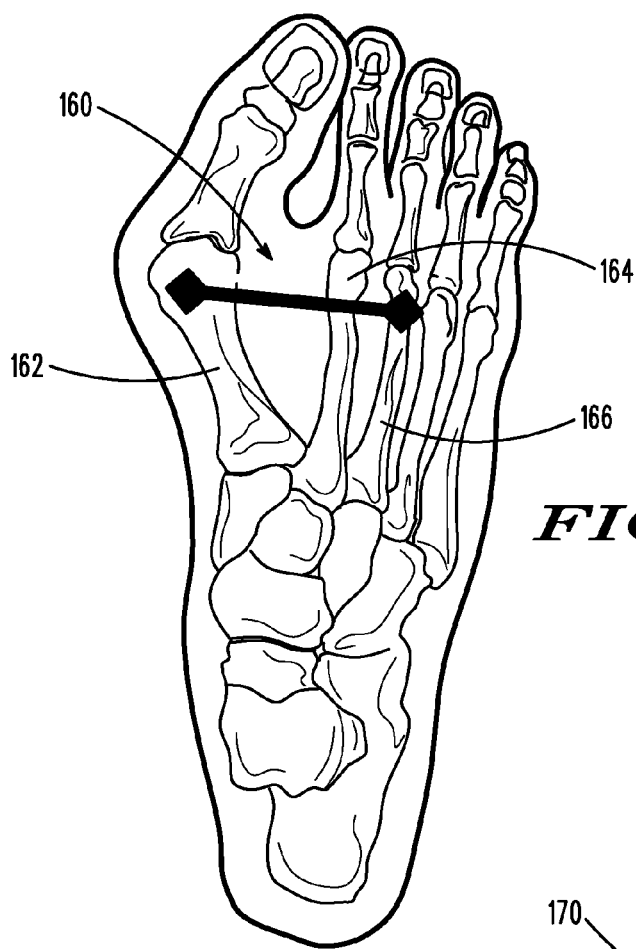
FIG. 8A is a schematic depiction of a further implantable bone deformity treatment device in a foot exhibiting hallux valgus, according to one embodiment.

For example, FIG. 8A depicts an alternative version of the device in which the device 160 is coupled not only to the first 162 and second 164 metatarsals, but to the third metatarsal 166 as well. In this embodiment, the attachment to the third metatarsal 166 can be advantageous because it distributes or spreads out the tightening force to another metatarsal, thereby reducing the force applied to the second metatarsal.

Figure 8B:
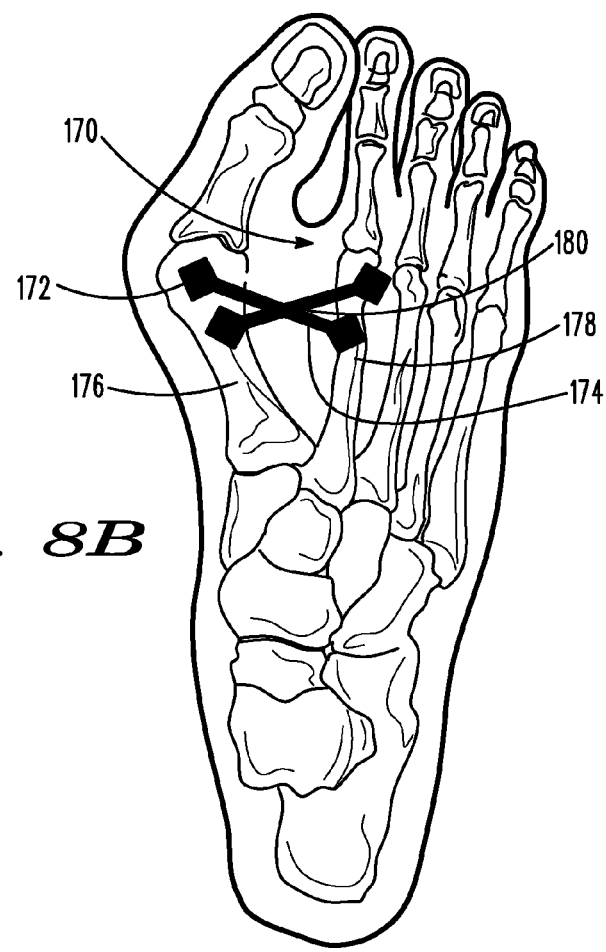
FIG. 8B is a schematic depiction of another implantable bone deformity treatment device in a foot exhibiting hallux valgus, according to another embodiment.

In another embodiment depicted in FIG. 8B, the system 170 includes two devices 172, 174, both of which are coupled to the first 176 and second 178 metatarsals. In the embodiment shown, the two devices exhibit an "X" or crossed configuration in which the two device 172, 174 appear to intersect when viewed from above as shown. In this implementation, the two devices 172, 174 are coupled to the metatarsals 176, 178 at different heights such that one of the two devices 172, 174 is positioned above the other. Alternatively, the two devices 172, 174 can be coupled to each other at the intersection point 180. In a further alternative, any "X" configuration is contemplated in which each of the two devices 172, 174 is coupled to the first and second metatarsals 176, 178 and the two form an "X" configuration. The two devices 172, 174 both separately apply tensioning force to the first 176 and second 178 metatarsals as described in other embodiments above, thereby distributing the force amongst four anchors instead of two.

Figure 8C:
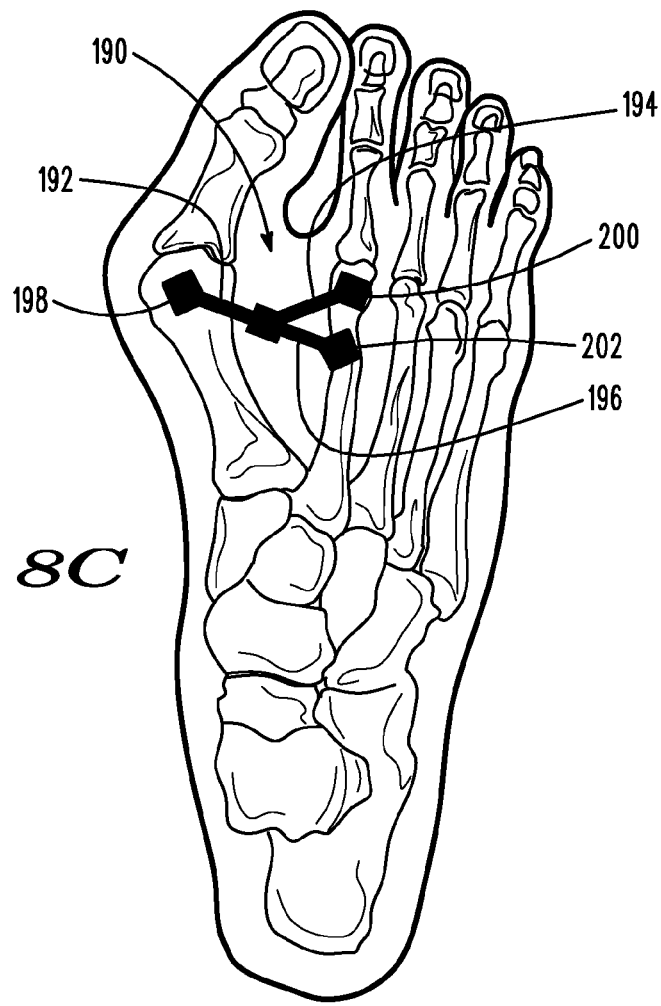
FIG. 8C is a schematic depiction of yet another implantable bone deformity treatment device in a foot exhibiting hallux valgus, according to a further embodiment.

In a further implementation as shown in FIG. 8C, the device 190 has a first leg 192 that is coupled to the first metatarsal 204 at a first anchor 198, and second 194 and third 196 legs that are coupled to the second metatarsal 206 at second 200 and third 202 anchors, respectively. Alternatively, the device 190 can be positioned such that the first leg 192 is coupled to the second metatarsal 206 and the second 194 and third 196 legs are coupled to the first metatarsal 204. In a further alternative, the device 190 has two legs that are connected to each other and the first metatarsal 204 at a single anchor, while each of the two legs have anchors at the other ends of the legs that are coupled at different points to the second metatarsal 206. In yet another alternative, the device 190 has two legs that are connected to each other and the second metatarsal 206 at a single anchor, while each of the two legs have anchors at the other ends of the legs that are coupled at different points to the first metatarsal 204. Thus, the device 190 distributes the force amongst three anchors instead of two.

Figure 9:
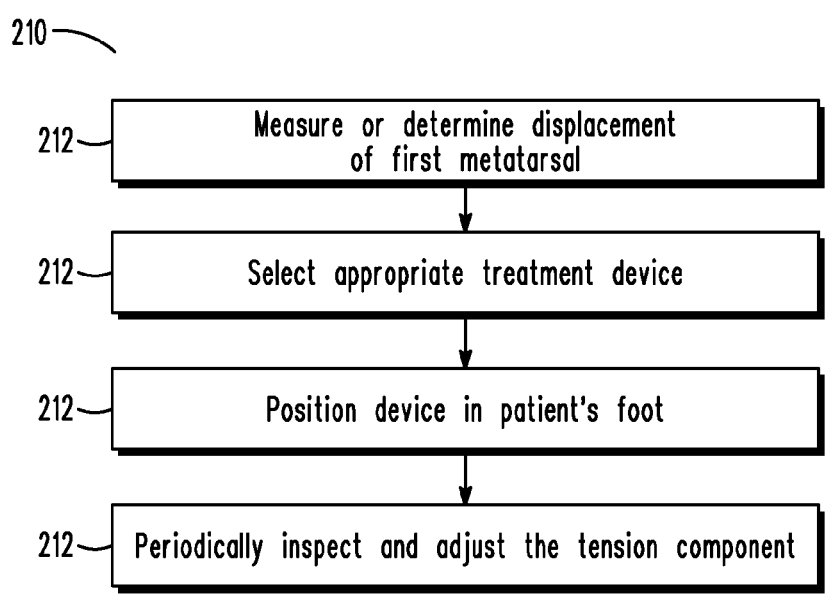
FIG. 9 depicts a flowchart illustrating a method of implanting a bone deformity treatment device, according to one embodiment.

The various embodiments described herein can be used in a method to treat hallux valgus 210, according to one embodiment depicted schematically in FIG. 9. In this method, the displacement of the first metatarsal is first measured or determined (block 212). The displacement can be determined using any known method. Based at least in part on the amount of displacement, the appropriate treatment device, such as one of the embodiments disclosed herein, is selected having a suitable length and tension profile (block 214). That is, according to one embodiment, a medical professional utilizes the first metatarsal displacement information to select a device that will best treat the displacement based in part on the dimensions of the patient's foot and the amount of displacement. Once the device has been selected, it is then positioned appropriately in the patient's foot (block 216). In one implementation, one anchor is coupled to the first metatarsal and a second anchor is coupled to the second metatarsal. In other embodiments, the second anchor or a third anchor is coupled to the third metatarsal. After correct positioning, the device can be periodically inspected and the dynamic tension component adjusted to optimize the treatment (block 218).

Although the present invention has been described with reference to preferred embodiments, persons skilled in the art will recognize that changes may be made in form and detail without departing from the spirit and scope of the invention.

What is claimed is:

1. A method of treating a bone deformity, comprising:
securing a first anchor to a first metatarsal bone;
securing a second anchor to a second metatarsal bone;
securing a dynamic tension component to the first and second anchors, wherein the dynamic tension component comprises a tension member and a bioabsorbable spacer and is configured to exert a first force capable of urging the first and second metatarsal bones toward each other upon removal of the bioabsorbable spacer; and
urging the first and second metatarsal bones toward each other over time with the dynamic tension component upon removal of the bioabsorbable spacer.

2. The method of claim 1, wherein securing the dynamic tension component to the first and second anchors is done such that, at the time of implantation, the dynamic tension component exerts a second force urging the first and second metatarsal bones toward each other prior to removal of the bioabsorbable spacer.

3. The method of claim 1, wherein removal of the bioabsorbable spacer occurs by absorption.

4. The method of claim 1, wherein the tension member is a polymeric material.

5. The method of claim 1, wherein the tension member is a spring.

6. A method of treating a bone deformity comprising:
securing a first anchor to a first bone;
securing a second anchor to a second bone;
securing a dynamic tension component to the first and second anchors, wherein the dynamic tension component comprises a bioabsorbable member, the dynamic tension component configured to reduce in length as the bioabsorbable member is absorbed; and
urging the first and second bones toward each other over time with the dynamic tension component as the dynamic tension component length is reduced.

7. The method of claim 6, wherein the length reduction occurs gradually.

8. The method of claim 6, wherein the length reduction occurs in quick steps.

9. The method of claim 6, wherein the dynamic tension component comprises multiple bioabsorbable members having different absorption rates.

10. The method of claim 6, wherein the bioabsorbable member is configured to maintain tension in the dynamic tension component prior to absorption of the bioabsorbable member.

11. The method of claim 6, wherein the bones are metatarsals.

12. A method of treating a bone deformity comprising:
securing a first anchor to a first metatarsal bone;
securing a second anchor to a second metatarsal bone;
securing a dynamic tension component to the first and second anchors such that the dynamic tension component is in a tensioned state, wherein the dynamic tension component exhibits elasticity; and
urging the first and second metatarsal bones toward each other over time with the dynamic tension component, wherein the dynamic tension component moves toward an untensioned state as the first and second metatarsal bones move toward each other,
wherein a length of the dynamic tension component changes at least 10% as the dynamic tension component moves toward the untensioned state,
wherein at least a portion of the dynamic tension component comprises a bioabsorbable component, wherein absorption of the bioabsorbable component moves the dynamic tension component toward the untensioned state.

13. The method of claim 12, wherein the urging the first and second metatarsal bones toward each other with the dynamic tension component further comprises:
urging the first and second metatarsal bones toward each other a first distance during a first time interval; and
urging the first and second metatarsal bones toward each other a second distance during a second later time interval.

14. The method of claim 12, wherein at least one of the first and second anchors is chosen from the group consisting of:
a sleeve configured to be disposed around a metatarsal bone;
a filament configured to be disposed around a metatarsal bone;
an anchor body having a length perpendicular to a length of the body, wherein the anchor body is configured to be deployed against a first side of a metatarsal bone, wherein a portion of the dynamic tension component is disposed through the metatarsal bone and further is coupled to the body on a second side of the metatarsal bone that is opposite the first side;
an anchor body having a length perpendicular to a length of the body, wherein the anchor body is configured to be disposed within an intramedullary canal of a metatarsal bone; and
an anchor body fixedly positioned in a top portion of a metatarsal bone.

15. A method of treating a bone deformity comprising:
securing a first anchor to a first bone;
securing a second anchor to a second bone;
securing a dynamic tension component to the first and second anchors such that the dynamic tension component is in a tensioned state, wherein the dynamic tension component exhibits elasticity; and
urging the first and second bones toward each other over time as the dynamic tension component moves toward art untensioned state, wherein the dynamic tension component moves toward an untensioned state as the first and second bones move toward each other, and wherein the dynamic tension component remains in a tensioned state when the bone deformity is fully treated,
wherein at least a portion of the dynamic tension component comprises a bioabsorbable component, wherein absorption of the bioabsorbable component moves the dynamic tension component toward the untensioned state.

16. The method of claim 12, wherein a rate of absorption of the bioabsorbable component controls the time over which the first and second metatarsal bones are urged toward each other.

17. The method of claim 15, wherein a length of the dynamic tension component changes at least 10% as the dynamic tension component moves toward the untensioned state.

18. The method of claim 15, wherein the urging the first and second bones toward each other with the dynamic tension component further comprises:
urging the first and second bones toward each other a first distance during a first time interval; and
urging the first and second bones toward each other a second distance during a second later time interval.

19. The method of claim 15, wherein a rate of absorption of the bioabsorbable component controls the time over which the first and second bones are urged toward each other.

20. The method of claim 15, wherein at least one of the first and second anchors is chosen from the group consisting of:
a sleeve configured to be disposed around a metatarsal bone;
a filament configured to be disposed around a metatarsal bone;
an anchor body having a length perpendicular to a length of the body, wherein the anchor body is configured to be deployed against a first side of a metatarsal bone, wherein a portion of the dynamic tension component is disposed through the metatarsal bone and further is coupled to the body on a second side of the metatarsal bone that is opposite the first side;
an anchor body having a length perpendicular to a length of the body, wherein the anchor body is configured to be disposed within an intramedullary canal of a metatarsal bone; and
an anchor body fixedly positioned in a top portion of a metatarsal bone.

* * * * *